US011498069B2

(12) United States Patent
Ferreira da Silva et al.

(10) Patent No.: US 11,498,069 B2
(45) Date of Patent: Nov. 15, 2022

(54) RAPID TESTING DEVICE FOR WASTEWATER ANALYSIS

(71) Applicant: INTERNATIONAL BUSINESS MACHINES CORPORATION, Armonk, NY (US)

(72) Inventors: Ademir Ferreira da Silva, São Paulo (BR); Daniel Vitor Lopes Marcondes Marçal, Rio de Janeiro (BR); Jaione Tirapu Azpiroz, Rio de Janeiro (BR); Matheus Esteves Ferreira, Rio de Janeiro (BR); Mathias B. Steiner, Rio de Janeiro (BR); Ricardo Luis Ohta, Sao Paulo (BR)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 284 days.

(21) Appl. No.: 17/008,611

(22) Filed: Aug. 31, 2020

(65) Prior Publication Data

US 2022/0062897 A1   Mar. 3, 2022

(51) Int. Cl.
*B01L 3/00* (2006.01)
*G01N 21/25* (2006.01)
(Continued)

(52) U.S. Cl.
CPC ... *B01L 3/502715* (2013.01); *B01L 3/502707* (2013.01); *G01N 21/251* (2013.01);
(Continued)

(58) Field of Classification Search
CPC ......... B01L 3/502715; B01L 3/502707; B01L 2200/10; B01L 2200/12; B01L 2300/021;
(Continued)

(56) References Cited

U.S. PATENT DOCUMENTS

2002/0106661 A1   8/2002   Virtanen
2013/0309679 A1   11/2013   Ismagilov et al.
(Continued)

FOREIGN PATENT DOCUMENTS

CN   103901025 A   7/2014
CN   104126120 A   10/2014
(Continued)

OTHER PUBLICATIONS

International Search Report and Written Opinion dated Sep. 28, 2021 in related application PCT/CN2021/104317; 11 pgs.
(Continued)

*Primary Examiner* — Jennifer Wecker
*Assistant Examiner* — Alea N. Martin
(74) *Attorney, Agent, or Firm* — Intelletek Law Group, PLLC; Gabriel Daniel, Esq.

(57) ABSTRACT

A rapid test device includes a micropad chip configured for a multi-parameter chemical testing of an input sample. A plurality of paper layers of the micropad chip are in fluid communication, including a sample absorption element, a filtering element configured to filter the input sample, and a sample distribution element configured to distribute the input sample received from the filtering element to a remainder of the plurality of paper layers. One or more reacting elements associated with the multi-parameter chemical testing of the input sample have one or more colorimetric reagents in fluid communication with the sample distribution element. A colorimetric result displaying element in fluid communication with the one or more reacting elements is configured to display a colorimetric result of the testing of the input sample with the at least one reacting element for a respective chemical test of the multi-parameter chemical testing.

19 Claims, 7 Drawing Sheets

(51) Int. Cl.
*G01N 21/78* (2006.01)
*G06T 7/90* (2017.01)
*G06K 19/06* (2006.01)
*G01N 33/18* (2006.01)

(52) U.S. Cl.
CPC .............. *G01N 21/78* (2013.01); *G01N 33/18* (2013.01); *G06K 19/06037* (2013.01); *G06T 7/90* (2017.01); *B01L 2200/10* (2013.01); *B01L 2200/12* (2013.01); *B01L 2300/021* (2013.01); *B01L 2300/025* (2013.01); *B01L 2300/069* (2013.01); *B01L 2300/0681* (2013.01); *B01L 2300/0864* (2013.01); *B01L 2300/161* (2013.01)

(58) Field of Classification Search
CPC ....... B01L 2300/025; B01L 2300/0681; B01L 2300/069; B01L 2300/0864; B01L 2300/161; G01N 21/251; G01N 21/78; G01N 33/18; G06K 19/06037; G06T 7/90
See application file for complete search history.

(56) References Cited

U.S. PATENT DOCUMENTS

| | | | |
|---|---|---|---|
| 2014/0295472 | A1 | 10/2014 | Shevkoplyas et al. |
| 2016/0274105 | A1* | 9/2016 | Whitesides ...... G01N 33/54386 |
| 2017/0067832 | A1 | 3/2017 | Ferrara, Jr. et al. |
| 2019/0118175 | A1 | 4/2019 | Kim et al. |
| 2019/0302008 | A1 | 10/2019 | Ohta et al. |

FOREIGN PATENT DOCUMENTS

| | | |
|---|---|---|
| CN | 104428651 A | 3/2015 |
| CN | 104975046 A | 10/2015 |
| CN | 105388149 A | 3/2016 |
| CN | 106442511 A | 2/2017 |
| CN | 106645123 A | 5/2017 |
| CN | 105181690 B | 3/2018 |
| CN | 108435266 A | 8/2018 |
| CN | 108704684 A | 10/2018 |
| CN | 109100525 A | 12/2018 |
| CN | 106698747 B | 4/2019 |
| CN | 110196249 A | 9/2019 |
| CN | 110320158 A | 10/2019 |

OTHER PUBLICATIONS

Cardoso, T. et al., "Colorimetric Determination of Nitrite in Clinical, Food and Environmental Samples Using Microfluidic Devices Stamped in Paper Platform"; The Royal Society of Chemistry (2013); vol. 00:1-3; 6 pgs.

Inês, M. et al., "Developments of Microfluidic Paper-Based Analytical Devices (µPADs) for Water Analysis: A Review" Talanta (2018); vol. 177; pp. 176-190.

Jayawardanea, B. et al., "Development of A Gas-Diffusion Microfluidic Paper-Based Analytical Device (µPAD) for the Determination of Ammonia in Wastewater Samples"; Analytical Chemistry (2015); 18 pgs.

Jayawardanea, B. et al., "Evaluation and Application of a Paper-Based Device for the Determination of Reactive Phosphate in Soil Solution"; Journal of Environmental Quality (2014); pp. 1091-1085.

Jayawardanea, B. et al., "Microfluidic Paper-Based Analytical Device (µPAD) for the Determination of Nitrite and Nitrate"; Analytical Chemistry (2014); 30 pgs.

Lopez-Ruiz, N. et al., "Smartphone-Based Simultaneous pH and Nitrite Colorimetric Determination for Paper Microfluidic Devices"; Analytical Chemistry (2014); vol. 86; pp. 9554-9562.

Noh, H. et al., "Fluidic Timers for Time-Dependent, Point-of-Care Assays on Paper"; Anal. Chem. (2010); vol. 82; pp. 8071-8078.

Ortiz-Gomez, I., et al., "Tetrazine-Based Chemistry for Nitrite Determination in A Paper Microfluidic Device"; Talanta (2016); vol. 160; pp. 721-728.

Phansi, P. et al., "Membraneless Gas-Separation Microfluidic Paper-Based Analytical Devices for Direct Quantitation of Volatile and Non-Volatile Compounds"; Analytical Chemistry (2016); 28 pgs.

Schwemmer, F., et al., "Microfluidic Timer for Timed Valving and Pumping in Centrifugal Microfluidics"; Royal Society of Chemistry (2012); 10 pgs.

Tirapu-Azpiroz, J. et al., "Modeling Fluid Transport in Two-Dimensional Paper Networks"; J. Micro/Nanolith. MEMS MOEMS (2018); vol. 17:2; 11 pgs.

Worsfold, P. et al., "Determination of Phosphorus in Natural Waters: A Historical Review"; Analytica Chimica Acta 918 (2016); 13 pgs.

* cited by examiner

RAPID TESTING DEVICE FOR WASTEWATER ANALYSIS

BACKGROUND

Technical Field

The present disclosure generally relates to testing devices for monitoring environmental conditions, and more particularly, to rapid testing devices.

Description of the Related Art

Today, there are increased efforts being made to monitor environmental conditions in a variety of agricultural and manufacturing operations. As the population increases worldwide, to ensure such operations do not adversely impact ecosystems is a salient element of providing for the health and safety of future generations.

However, the collecting and transmitting of samples to laboratories for analysis to monitor environmental conditions is a slow and costly process. For example, conventional monitoring often relies on titrimetric, electrometric, turbimetric, nephelometric, or colorimetric protocols carried out in a laboratory. The use of portable kits is less costly, but involves careful preparation steps and thorough cleaning of instrumentation after each use. There may also be inherent logistics issues due to the location of agricultural and manufacturing operations that further increase the cost and complexity of monitoring the environmental conditions. There is a need to perform rapid testing in various fields, particularly to verify compliance with discharge standards set in environmental compliance rules and regulations.

SUMMARY

According to various embodiments, a rapid test device and a method of manufacture are provided herein that provide for the inexpensive testing of chemical compounds in liquids in a rapid and simple manner. The results can be determined quickly without a need for a time-consuming laboratory analysis.

In one embodiment, a rapid test device includes a micro paper-based analytical device (micropad) chip configured for a multi-parameter chemical testing of an input sample. A plurality of paper layers of the micropad chip are in fluid communication including a sample absorption element, a filtering element configured to filter the input sample, and a sample distribution element configured to distribute the input sample received from the filtering element to a remainder of the plurality of paper layers. One or more reacting elements associated with the multi-parameter chemical testing of the input sample have one or more colorimetric reagents in fluid communication with the sample distribution element. A colorimetric result displaying element in fluid communication with the one or more reacting elements is configured to display a colorimetric result of the testing of the input sample with the at least one reacting element for a respective chemical test of the multi-parameter chemical testing. This structure provides an advantage in providing a fast and accurate way to test that does not require several days of analysis at a laboratory. The presence of multiple chemical compounds and their various concentrations can be readily analyzed by an image of the test result.

In one embodiment, the plurality of the paper layers are coated with a hydrophobic material configured to provide one or more hydrophilic channels on the paper layers. The coatings can be constructed in view of the types of input samples being tested and the paper used.

In one embodiment, a timer element is configured to indicate a predetermined time period at which an analysis of the input sample is complete. Rather than having to look at an actual timepiece, through the use of a timing channel and a visual indicator, a quick and easy indicator is provided to let a user know that the testing is complete. An image of the test result can be provided to an image processor for analysis. A color correction element is configured to display the input sample to determine whether the colorimetric result is to be adjusted based on a turbidity of the input sample. The accuracy of the colorimetric result is enhanced through the color correction element when the sample includes contaminants, debris, etc., that can skew the shade of the test result being displayed.

In one embodiment, the colorimetric result displaying element is configured to display a color shade that corresponds to a concentration of a particular chemical in the input sample. The various shades and their associated concentration levels can be stored in a table for a fast determination regarding concentration, without, for example, performing a more complex titer evaluation.

In one embodiment, the micropad chip is configured to test for a concentration of excess nutrients and pH in water. The one or more colorimetric reagents are customized for each test of the multi-parameter chemical testing. The multi-parameter testing ability by the rapid testing device provides a fast result to test for multiple chemical compounds and their concentrations in a substantially simultaneous manner, saving time and expenses.

In one embodiment, the micropad chip is configured to test for a concentration of at least one or more of phosphorous, and a convertible form of nitrogen. These particular chemical compounds tend to be associated in excess with agricultural operations. Such testing is salient to provide that operations comply with environmental regulations.

In one embodiment, the plurality of reacting elements associated with the multi-parameter chemical testing of the input sample is configured for a multi-step chemical reagent testing including a first reacting element having the one or more colorimetric reagents corresponding to at least a single-step and a double-step chemical reaction processes, and a second reacting element having the one or more colorimetric reagents corresponding to a second stage of the double-step chemical reaction. The ability to perform a single-step, a double-step, and even a triple-step testing with a single rapid test device provides a savings in time and increased testing efficiency and flexibility.

In one embodiment, the micropad chip is configured to test for a concentration of chemicals in wastewater associated with one or more of industrial drainage, hydraulic fracking and urban sewage. Such wastewater pollutants are a major concern for environmental safety.

In one embodiment, a cover element is arranged on at least a portion of the micropad chip, wherein the cover includes one or more visual identifications associated with the rapid testing device including an area configured for display of the colorimetric result displaying element.

In one embodiment, a portion of the cover element includes user instructions and manufacturing information.

In one embodiment, the one or more visual identifications of the cover element includes a Quick Response (QR) code having a device identifying code, and marks configured for image processing of the colorimetric result displaying element.

In one embodiment, the one or more visual identifications of the cover element includes a color reference for image processing of the colorimetric result displaying element.

In one embodiment, the cover element is constructed of a paperboard, and includes a front and a back.

In one embodiment, the colorimetric result displaying element is configured to display for capture by a camera the colorimetric result of the testing of the input sample with the at least one reacting element and the color reference.

According to one embodiment, a method of manufacturing a rapid test device for multi-parameter chemical testing of an input sample includes providing a micropad chip having a plurality of paper layers configured with a hydrophobic material arranged to provide one or more hydrophilic channels. The plurality of paper layers are configured for respective functions by providing a sample absorption element layer configured to receive an input sample, arranging a filtering element layer in fluid communication with the sample absorption element, and distributing the input sample received from the filtering element to a remainder of the plurality of paper layers by a sample distribution element layer. A plurality of reacting elements layers are provided, the reacting elements layers are associated with the multi-parameter chemical testing of the input sample with one or more colorimetric reagents in fluid communication with the filtering element. A colorimetric result displaying element layer in fluid communication with the plurality of reacting elements is provided to display a colorimetric result of the testing of the input sample with one or more of the plurality of reacting elements.

These and other features will become apparent from the following detailed description of illustrative embodiments thereof, which is to be read in connection with the accompanying drawings.

BRIEF DESCRIPTION OF THE DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all the components or steps that are illustrated. When the same numeral appears in different drawings, it refers to the same or like components or steps.

DETAILED DESCRIPTION

Overview

In the following detailed description, numerous specific details are set forth by way of examples to provide a thorough understanding of the relevant teachings. However, it should be apparent that the present teachings may be practiced without such details. In other instances, well-known methods, procedures, components, and/or circuitry have been described at a relatively high-level, without detail, to avoid unnecessarily obscuring aspects of the present teachings.

For example, some of the most productive chains of agriculture that ensure an adequate food supply are also responsible for the generation of volumes of waste having high concentrations of organic matter and nutrients. Nitrogen and phosphorus are two examples of organic matter associated with farming that in large quantities cannot be entirely absorbed by the soil, and require treatment prior to their discharge into rivers and lakes. Nitrogen and phosphorous appear in wastewater in different forms. Nitrogen can be found in wastewater in the form of ammonia (in equilibrium with ammonium), organic nitrogen, nitrate and nitrate. Phosphorus can exist in wastewater in the form of phosphates. The excessive amounts of nitrogen and phosphorous has deleterious effects on surrounding bodies of water, and all the wildlife reliant on such water.

In an illustrative embodiment, the present disclosure relates to a rapid test device and a method for testing of wastewater. A paper-based rapid test device is configured for measuring the excess nutrient concentration using colorimetric reagents.

Reference now is made in detail to the examples illustrated in the accompanying drawings and discussed below.

Example Architecture

Figure 1:
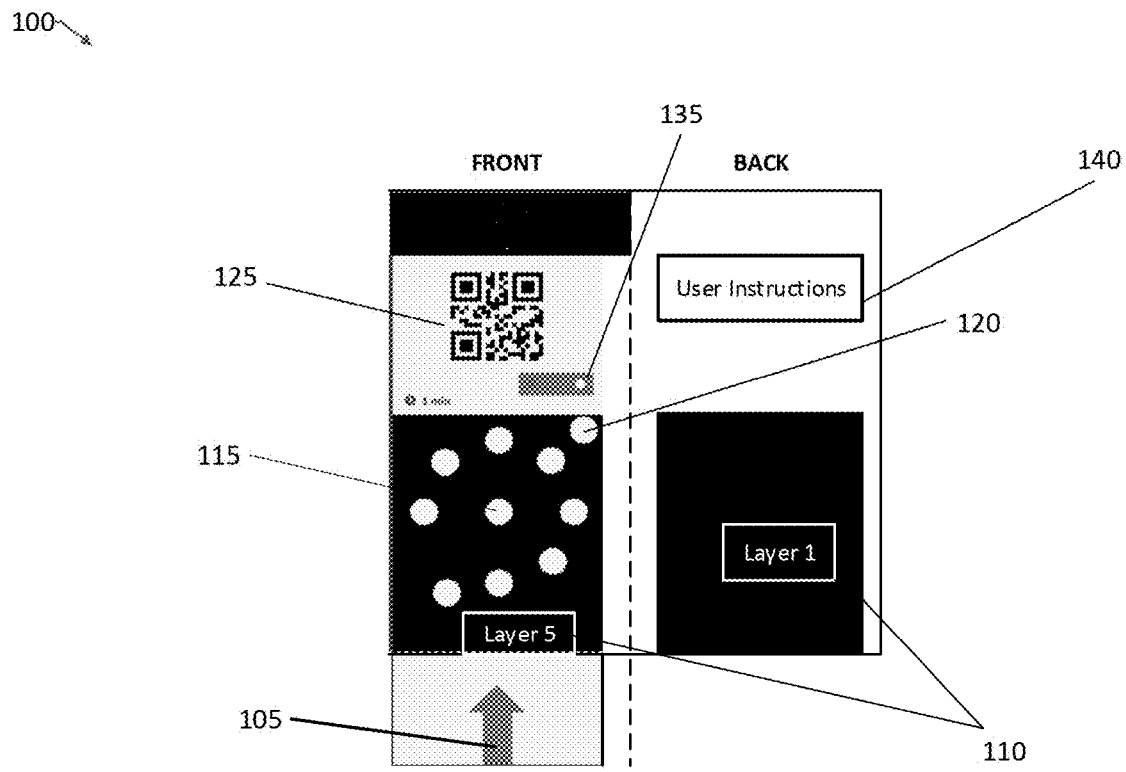
FIG. 1 illustrates an overview of a rapid testing device, consistent with an illustrative embodiment.

FIG. 1 illustrates an overview of a rapid testing device 100, consistent with an illustrative embodiment. It is to be understood that the rapid testing device shown is provided for illustrative purposes, and the appended claims are not limited to the illustration shown and described. To facilitate the understanding of the description, both the front and back of the cover elements of the rapid testing device 100 are shown. The paper micropad may be covered by the front cover only, or can be housed within the front and the back covers.

The rapid testing device 100 includes a sample absorption element 105. In the illustrative embodiment, the sample absorption element 105 extends from the rapid testing device to facilitate dipping a least a portion of the sample absorption element into an input sample.

The sample absorption element 105 is part of the micropad chip (see FIG. 2) used in the rapid testing device 100. In this illustrative embodiment, the micropad chip includes in its construction five paper-based layers 110. However, the rapid testing device is not limited to such construction, and fewer layers, or more layers, may be used. The "layer 5" of the paper-based layers 110 displays the reactive output of the input sample with various colorimetric reagents that show the presence and the concentration level of a plurality of chemical compounds. A background color correction element 115 is provided on the layer 5 to assist in the accuracy of the display. For example, if the input sample is turbid, or has a large amount of impurities, the colorimetric results may be skewed because the test results may appear to be darker. The background color correction element serves as an integrity check, and if there is a discoloration based on a turbid sample, correction action may be taken by an image processing system that analyzes the image of the testing device to determine a result.

In one non-limiting embodiment, the timing channel 120 changes color to indicate an optimum or recommended time after dipping the sample input absorption element 105 into the sample. An image of the front of the rapid testing device can be captured by a smartphone or other device. The smartphone or other device may relay the image information to, for example, a server to determine the concentrations of several chemical compounds (e.g., multi-parameter testing), and provide this information to the appropriate designees. Alternatively, the smartphone may have an app that determines the test results in situ, for example, by tables that have chemicals and concentrations based on the colors and shades of the output of the rapid test device 100, with polynomial equations that describe relations between color channels and concentrations or leveraging machine learning algorithms (e.g.: logistic regression, K-nearest neighbors, etc.) to estimate the concentration, using color channels as information input.

With continued reference to FIG. 1, the rapid test device may include identification information 125, such as a bar code, or a Quick Response (QR) code. The type of tests, the location, the manufacturer, area being tested, etc., are all some of the information that may be listed in the QR code 125. A color reference 135 may be provided for image processing, for example, in the event that the image of the test device captured by a camera may have variations in the camera capabilities, environmental lighting conditions, etc., that could otherwise introduce an inaccuracy into the tests. An image processing system (not shown) may correct the captured color readings based on a comparison to the color reference 135.

The rapid test device may include user instructions 140, for example, on the back of the rapid test device or a rear cover. It is to be understood that the rapid test device according to the present disclosure is not limited to including the instructions as shown in FIG. 1.

Figure 2:
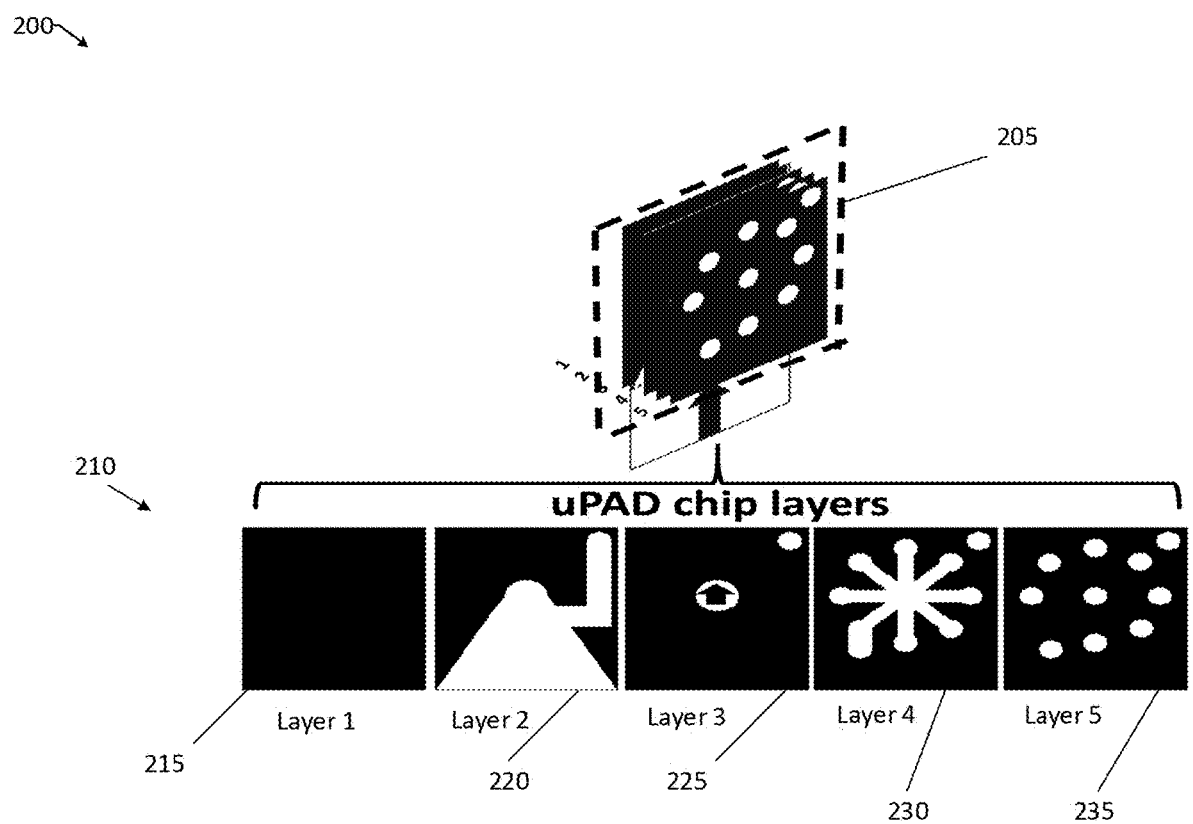
FIG. 2 illustrates a paper-based micropad of the rapid testing device shown in FIG. 1, consistent with an illustrative embodiment.

FIG. 2 illustrates a paper-based micropad 205 of the rapid testing device shown in FIG. 1, consistent with an illustrative embodiment. In operation in a rapid testing device, the micropad 205 typically has layers folder/stack upon each other. However, the micropad chip layers 210 are also shown in an unstacked/unfolded position for ease of description.

The first layer is a sample absorption element 215 that serves as a dip input, for example, to load the input sample into the rapid test device for analysis. The second layer is a filtering element 220 that is in fluid communication with the sample absorption element 215. The filtering element 220 may be used to remove impurities that are not being tested for and that may interfere with the passage of the input sample through the micropad.

The third layer is a sample distribution element 225. The sample distribution element 225 distributes the input sample received from the filtering element to a remainder of the plurality of paper layers.

The fourth layer is a reaction element layer 230 that is configured for multi-parameter chemical testing of the input sample. The reaction layer 230 includes one or more colorimetric reagents in fluid communication with the sample distribution element 225. It is to be understood that multiple reaction element layers may be provided in the micropad 205, and in such construction, the multiple reaction element layers may be referred to with ordinal terminology (e.g., first, second, etc.).

The fifth layer is a colorimetric result displaying element 235 in fluid communication with the reacting element layer 230. The result displaying element 235 is configured to display a colorimetric result of the testing of the input sample by the reacting element layer 230 for a respective chemical test of the multi-parameter chemical testing.

Figure 3:
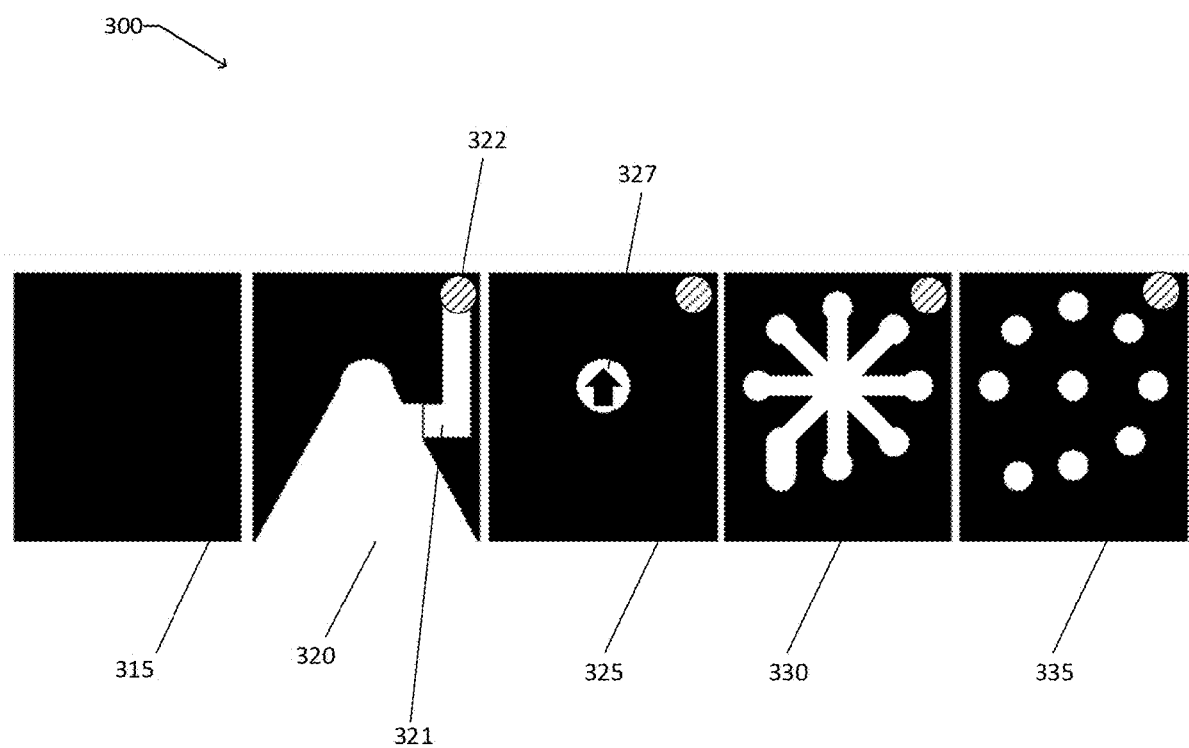
FIG. 3 illustrates the layers of the paper-based micropad, consistent with an illustrative embodiment.

FIG. 3 illustrates the layers 300 of the paper-based micropad, consistent with an illustrative embodiment. Similar to FIG. 2, shown in FIG. 3 is a sample absorption element 315 that can be dipped into the input sample. The filtering element 320 is in fluid communication with the sample absorption element 315, and serves to filter the input sample. It is noted that the filtering element 320 in this illustrative embodiment includes a timing channel 321. A timing indication 322 indicates that the testing is complete. The sample distribution element 325, with a passageway 327 indicated by the arrow and the reacting element 330, and the result displaying element 335, are also similar to the micropad shown in FIG. 2. The timing element 322, which is also displayed by the result displaying element 335, allows a tester to know that the analysis is complete.

Figure 4:
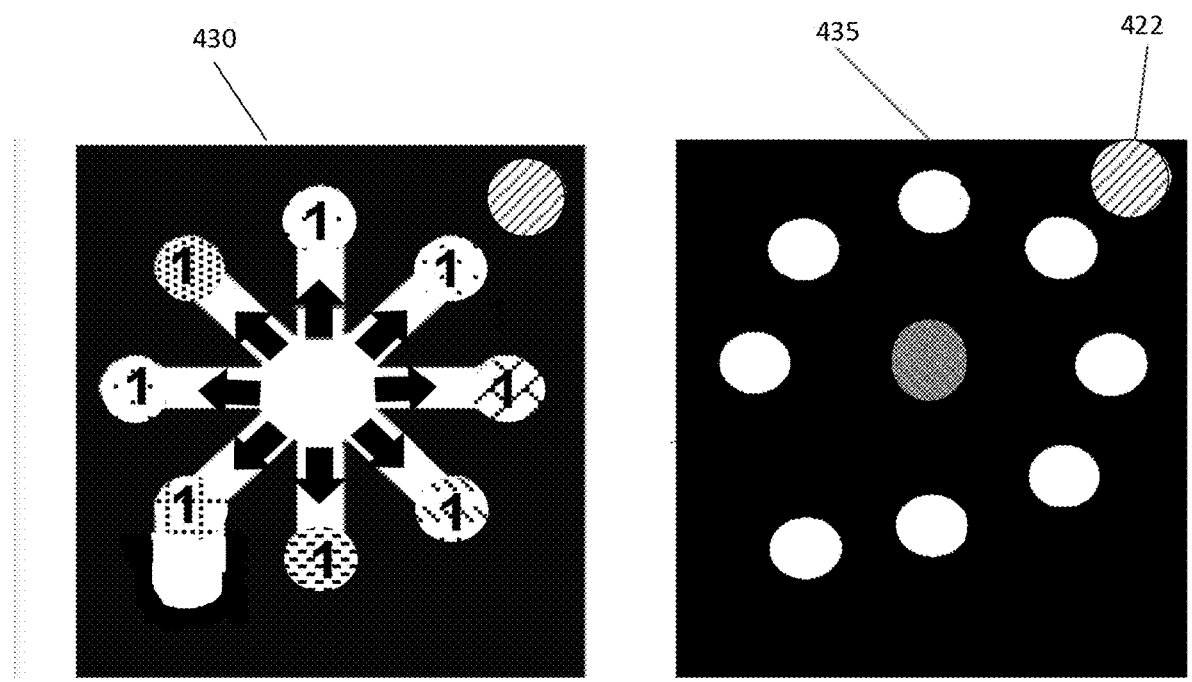
FIG. 4 illustrates some layers of the micropad used in a single step chemical reagent to determine the pH of an input sample, consistent with an illustrative embodiment.

FIG. 4 illustrates some layers of the micropad used in a single-step chemical reagent operative to determine a pH of an input sample, consistent with an illustrative embodiment. Timing element 422 is shaded to show that the testing is complete. The reacting element 430 shows various shades of tests performed on an input sample. For example, a pH course range using a universal reagent indicator in ethanol can result in various displays according to the pH. For example, methyl yellow, methyl red, bromothymol blue, thymol blue and phenophthlein can be used to determine a pH coarse range. Bromothymol blue can indicate a pH range from 6 to 7.6. In addition, a pH low range can be indicated by bromocresol green in ethanol. There may be little or no second reacting element activity indicated by the display element 435.

Figure 5:
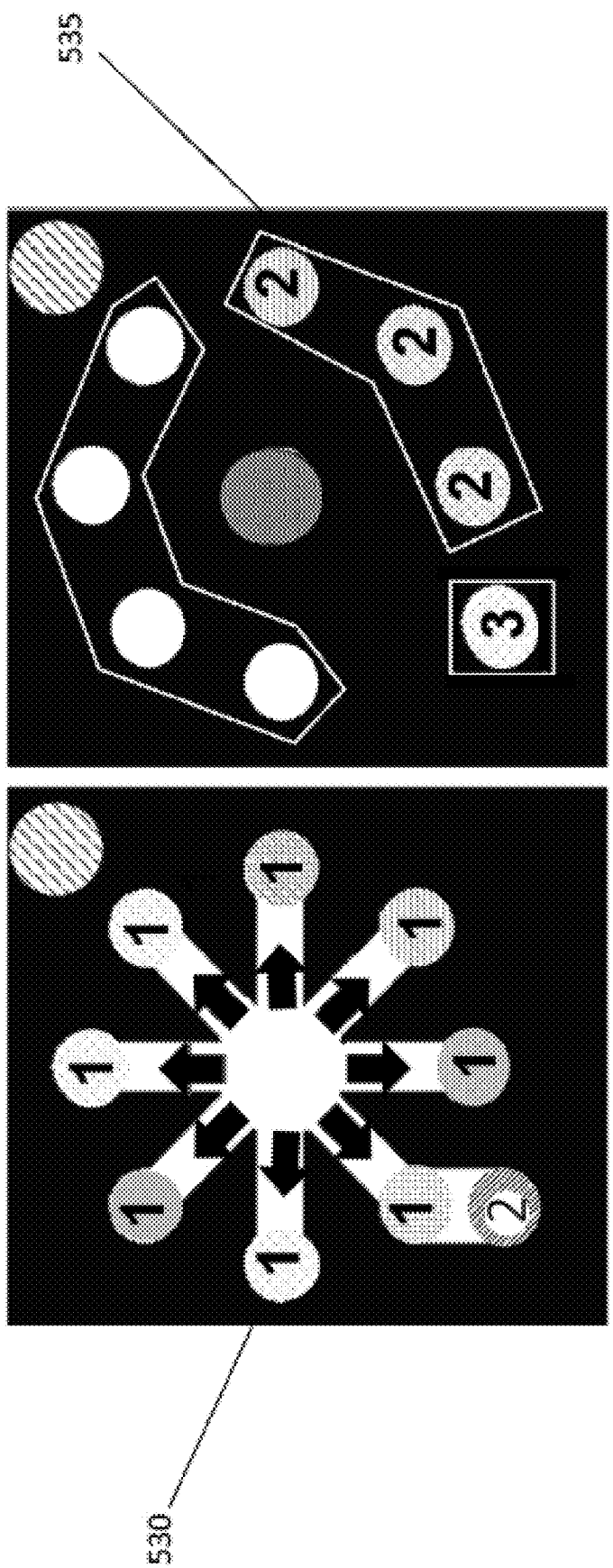
FIG. 5 illustrates some layers of the micropad used in double-step and triple-step chemical reagents, consistent with an illustrative embodiment.

FIG. 5 illustrates some layers of the micropad used in double-step and triple-step chemical reagents, consistent with an illustrative embodiment. The reacting element 530 shows double-step reagents, and the display element 535 shows double-step reagents and triple-step reagents, as indicated by the corresponding numbers. In FIG. 5, double-step reagents can be used for the detection of Phosphate, Nitrite and Ammonia, and a triple-step reagent can be used for the detection of Nitrate levels.

With regard to Phosphate detection, in one embodiment, the reagents include: Reagent 1 is a mixture of ammonium heptamolybdate tetrahydrate, potassium antimony (III) tartrate hydrate in sulfuric acid. The Reagent 2 is ascorbic acid.

With regard to Nitrite detection, in one embodiment, the reagents include: a Reagent 1 is N-(1-Naphthyl) ethylenediamine. The Reagent 2 is Sulfanilamide.

With regard to Nitrate detection (triple-step), in one embodiment, a Reagent 1 is a Zinc suspension, a Reagent 2 is N-(1-Naphthyl) ethylenediamine, and a Reagent 3 is Sulfanilamide.

With regard to Ammonia detection, in one embodiment, Reagent 1 is Potassium hydrogen phthalate (KHPth), and Reagent 2 is Bromocresol Purple. The colorimetric result of the double-step and triple-step reagents are shown in 535.

Figure 6:
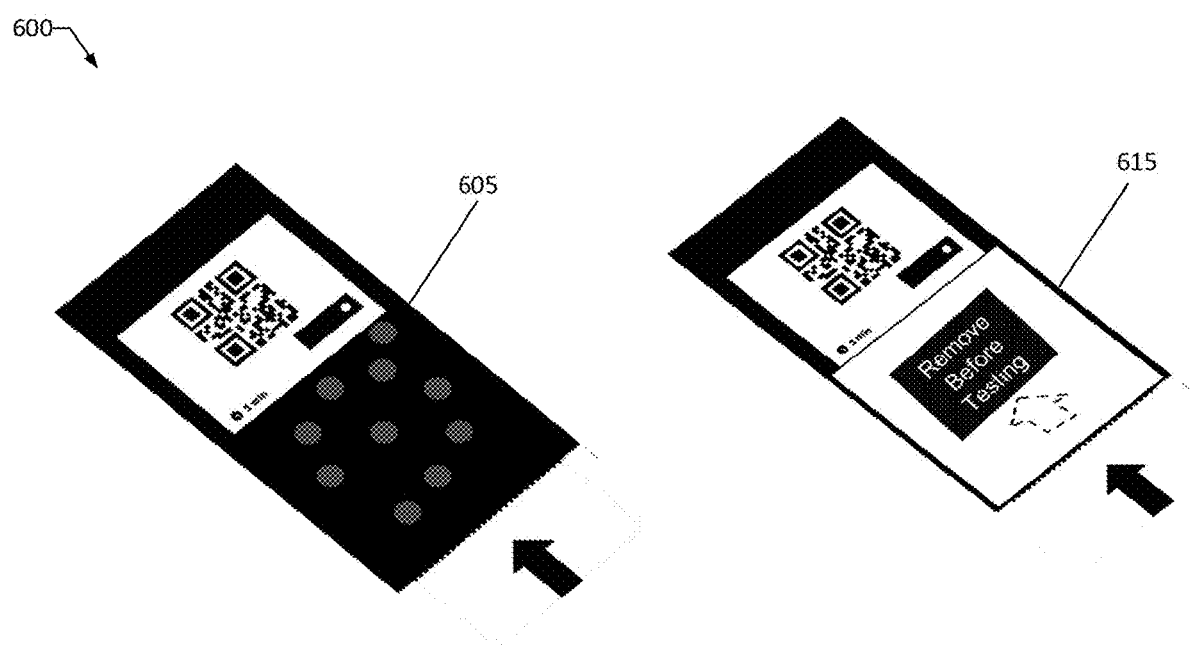
FIG. 6 illustrates examples of protector layers of the rapid testing device, consistent with an illustrative embodiment.

FIG. 6 illustrates examples of protector layers 600 of the rapid testing device, consistent with an illustrative embodiment. The protective layer 605 is a transparent covering that remains on whereas the protective layer 615 is to be peeled off prior to testing the input sample. It is to be understood that the protector layers of the rapid testing device are not limited to the aforementioned examples shown in FIG. 6.

Example Processes

Figure 7:
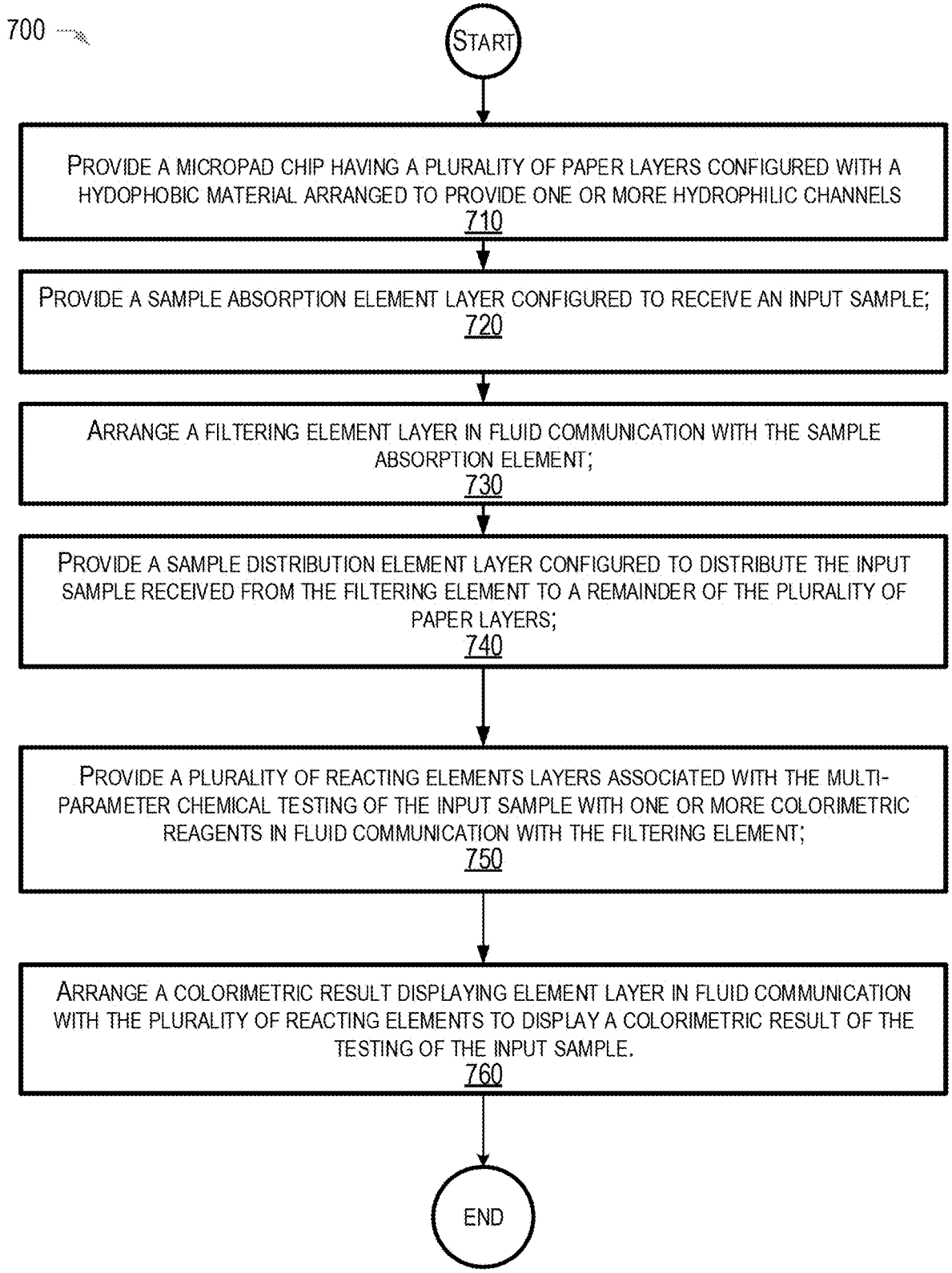
FIG. 7 is a flowchart illustrating a method of manufacturing a rapid test device, consistent with an illustrative embodiment.

With the foregoing overview of the example architecture, it may be helpful now to consider a high-level discussion of an example process. To that end, FIG. 7 is a flowchart 700 of a manufacturing process of a rapid testing device shown in FIGS. 1, 2 and 3. More specifically, FIG. 7 is a flowchart illustrating a method of manufacturing a rapid test device, consistent with an illustrative embodiment.

At operation 710, a micropad is provided with a plurality of paper layers with a hydrophobic material configured to provide hydrophilic channels. The micropad is configured to contain a plurality of reacting element layers with a plurality of colorimetric reagents embedded in the fibers of the paper channel and in fluid communication with the sample distribution element. The construction of channels on the paper-based layers permits multi-parameter rapid testing of multiple chemical compounds from a single test device.

At operation 720, a sample absorption element layer is configured to receive an input sample. As shown in FIG. 1, the sample absorption element layer may extend from the rapid testing device to facilitate dipping into an input sample.

At operation 730, a filtering element is arranged in fluid communication with the sample absorption element. While in FIGS. 2 and 3, the filtering element is shown to have a substantial V-shape, the rapid testing device is not limited thereto. The filtering element can remove impurities from the sample that are not being tested for, but may impede the flow of the input sample through the micropad layers.

At operation 740, a sample distribution element layer is provided to distribute the filtered input sample to a remainder of the plurality of paper layers for testing. FIG. 3 shows the sample distribution element layer 325 with the passageway 327 in the center of the layer 3, but such a construction is provided for illustrative purposes and it can be arranged in another portion of the micropad as well.

At operation 750, a plurality of reacting element layers associated with multi-parameter chemical testing of the input sample are provided. The reacting element layers receive the input sample and colorimetric reagents to indicate the presence and concentration of various chemicals in the input sample.

At operation 760, a colorimetric result displaying element is arranged in fluid communication with the plurality of reacting elements to display a colorimetric result of the testing of the input sample. The description associated with FIGS. 4 and 5 discusses that single-step, double-step, and triple-step reagent testing can be performed by the rapid testing device.

Although the basic method of manufacturing ends at operation 760, there can be additional operations such as including a timer element in the paper-based layers, arranging the micropad in cover elements, and marking the cover elements with identification information such as QR codes and color reference information.

CONCLUSION

The descriptions of the various embodiments of the present teachings have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing has described what are considered to be the best state and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The components, steps, features, objects, benefits and advantages that have been discussed herein are merely illustrative. None of them, nor the discussions relating to them, are intended to limit the scope of protection. While various advantages have been discussed herein, it will be understood that not all embodiments necessarily include all advantages. Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Numerous other embodiments are also contemplated. These include embodiments that have fewer, additional, and/or different components, steps, features, objects, benefits and advantages. These also include embodiments in which the components and/or steps are arranged and/or ordered differently.

While the foregoing has been described in conjunction with exemplary embodiments, it is understood that the term "exemplary" is merely meant as an example, rather than the best or optimal. Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments have more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. A rapid test device comprising:
   a micropad chip configured for a multi-parameter chemical testing of an input sample, the micropad chip having a plurality of paper layers in fluid communication including:
   a sample absorption element configured to receive an input sample;
   a filtering element in fluid communication with the sample absorption element and configured to filter the input sample;
   a sample distribution element configured to distribute the input sample received from the filtering element to a remainder of the plurality of paper layers;
   one or more reacting elements associated with the multi-parameter chemical testing of the input sample that include one or more colorimetric reagents in fluid communication with the sample distribution element;
   a colorimetric result displaying element in fluid communication with at least one of the one or more reacting elements and configured to display a colorimetric result of the testing of the input sample by the at least one reacting element for a respective chemical test of the multi-parameter chemical testing;
   and wherein the micropad chip is configured to test for a concentration of excess nutrients and a pH in water; and the one or more colorimetric reagents are customized for each test of the multi-parameter chemical testing.

2. The rapid test device according to claim 1, wherein the plurality of paper layers are coated with a hydrophobic material configured to provide one or more hydrophilic channels.

3. The rapid testing device according to claim 2, further comprising:
   a timer element configured to indicate a predetermined time period at which an analysis of the input sample is complete, and
   a color correction element configured to display the input sample to determine whether the colorimetric result is to be adjusted based on a turbidity of the input sample.

4. The rapid testing device according to claim 3, wherein the colorimetric result displaying element is configured to display a color shade that corresponds to a concentration of a particular chemical in the input sample.

5. The rapid testing device according to claim 1, wherein the micropad chip is configured to test for a concentration of at least one of phosphorous or a convertible form of nitrogen.

6. The rapid testing device according to claim 5, wherein the plurality of reacting elements associated with the multi-parameter chemical testing of the input sample are configured for a multi-step chemical reagent testing comprising:
   a first reacting element having the one or more colorimetric reagents corresponding to at least a single-step and a double-step chemical reaction processes; and
   a second reacting element having the one or more colorimetric reagents corresponding to a second stage of the double-step chemical reaction.

7. The rapid testing device according to claim 3, wherein the micropad chip is configured to test for a concentration of chemicals in wastewater associated with one or more of industrial drainage, hydraulic fracking, or urban sewage.

8. The rapid testing device according to claim 3, further comprising a cover element arranged on at least a portion of the micropad chip, wherein the cover element includes one or more visual identifications associated with the rapid testing device including an area configured for display of the colorimetric result displaying element.

9. The rapid testing device according to claim 8, wherein a portion of the cover element includes user instructions and manufacturing information.

10. The rapid testing device according to claim 8, wherein the one or more visual identifications of the cover element include a Quick Response (QR) code having a device identifying code, and marks configured for image processing of the colorimetric result displaying element.

11. The rapid testing device according to claim 8, wherein the one or more visual identifications of the cover element include a color reference for image processing of the colorimetric result displaying element.

12. The rapid testing device according to claim 8, wherein the cover element comprises a paperboard, and includes a front and a back.

13. The rapid testing device according to claim 11, wherein the colorimetric result displaying element is configured to display for capture by a camera the colorimetric result of the testing of the input sample with the at least one reacting element and the color reference.

14. A method of manufacturing a rapid test device for multi-parameter chemical testing of an input sample, the method comprising:
   providing a micropad chip having a plurality of paper layers configured with a hydrophobic material arranged to provide one or more hydrophilic channels;
   configuring the plurality of paper layers for respective functions by:
   providing a sample absorption element layer configured to receive an input sample;
   arranging a filtering element layer in fluid communication with the sample absorption element; distributing the input sample received from the filtering element to a remainder of the plurality of paper layers by a sample distribution element layer;
   providing a plurality of reacting elements layers associated with the multi-parameter chemical testing of the input sample with one or more colorimetric reagents in fluid communication with the filtering element wherein the plurality of reacting elements test for a concentration of excess nutrients and a pH in water; and
   displaying a colorimetric result of the testing of the input sample with one or more of the plurality of reacting elements by arranging a colorimetric result displaying element layer in fluid communication with the plurality of reacting elements.

15. The method according to claim 14, further comprising indicating a predetermined time period at which an analysis of the input sample is complete by a timer element layer.

16. The method according to claim 15, further comprising providing a cover arranged on at least a portion of the micropad chip, wherein the cover includes one or more visual identifications associated with the rapid testing device including an area configured for display of the colorimetric result displaying element.

17. The method according to claim 16, wherein the providing of a plurality of reacting elements layers associated with the multi-parameter chemical testing further comprises:
   configuring for a multi-step chemical reagent testing by providing a first reacting element with the one or more colorimetric reagents corresponding to at least a single-step and a double-step chemical reaction processes; and providing a second reacting element having the one or more colorimetric reagents corresponding to a second stage of the double-step chemical reaction.

18. A rapid test device for measuring excess nutrients and pH in water, comprising: a plurality of paper-based layers comprising:

a sample absorption element layer configured to receive an input sample;

a filtering element layer configured to filter the input sample received from the sample absorption element; a sample distribution element layer configured to distribute the input sample received from the filtering element to a remainder of a plurality of paper layers;

one or more reacting elements layers configured for a multi-parameter chemical testing of the input sample received from the sample distribution element, the one or more reacting elements including one or more colorimetric reagents configured to identify a concentration of excess nutrients including at least one or more of phosphorous, or a convertible form of nitrogen and further configured to test a pH in the water;

a colorimetric result displaying element layer in fluid communication with at least one of the one or more reacting elements and configured to display a colorimetric result of the testing of the input sample with the at least one reacting element for a respective chemical test of the multi-parameter chemical testing; a timer element layer configured to indicate the testing is complete; and a color reference configured for image processing of the displayed colorimetric result.

19. The rapid-test device according to claim 18, wherein the plurality of paper-based layers are formed as a micropad chip configured to perform the multi-parameter testing, and are coated with a hydrophobic material configured to provide one or more hydrophilic channels; and the rapid test device further comprises:

a cover element arranged on at least a portion of the micropad chip, wherein the cover element includes one or more visual identifications associated with the rapid testing device including an area configured for display of the colorimetric result displaying element.

* * * * *